（12）United States Patent
Haraguchi et al.

(10) Patent No.: US 8,882,012 B2
(45) Date of Patent: Nov. 11, 2014

(54) CELL ISOLATION APPARATUS

(75) Inventors: Yuji Haraguchi, Tokyo (JP); Tatsuya Shimizu, Tokyo (JP); Teruo Okano, Tokyo (JP); Takahiro Shioyama, Tokyo (JP); Akane Suzuki, Tokyo (JP); Sunao Takeda, Tokyo (JP)

(73) Assignees: Nihon Kohden Corporation, Tokyo (JP); Tokyo Women's Medical University, Tokyo (JP)

( * ) Notice: Subject to any disclaimer, the term of this patent is extended or adjusted under 35 U.S.C. 154(b) by 273 days.

(21) Appl. No.: 13/217,437

(22) Filed: Aug. 25, 2011

(65) Prior Publication Data

US 2012/0052559 A1 Mar. 1, 2012

(30) Foreign Application Priority Data

Aug. 27, 2010 (JP) ................. 2010-191035

(51) Int. Cl.
*B02C 18/00* (2006.01)
*B02C 13/28* (2006.01)
*C12M 1/33* (2006.01)
*G01N 1/28* (2006.01)
*C12M 1/00* (2006.01)

(52) U.S. Cl.
CPC .............. *G01N 1/286* (2013.01); *C12M 45/02* (2013.01); *G01N 2001/2866* (2013.01); *C12M 47/04* (2013.01)
USPC ........ 241/199.12; 241/277; 241/2; 241/262.1

(58) Field of Classification Search
USPC ................. 241/2, 21, 199.12, 36, 277, 282.1, 241/282.2
See application file for complete search history.

(56) References Cited

U.S. PATENT DOCUMENTS

| 3,666,187 | A | | 5/1972 | Norris |
|---|---|---|---|---|
| 4,028,190 | A | | 6/1977 | McAleer et al. |
| 5,064,124 | A | * | 11/1991 | Chang ............................ 241/33 |
| 5,261,612 | A | * | 11/1993 | Ftaiha ............................. 241/2 |
| 5,786,207 | A | | 7/1998 | Katz et al. |
| 6,391,541 | B1 | * | 5/2002 | Petersen et al. ................... 435/5 |
| 7,048,211 | B2 | * | 5/2006 | Bratcher et al. ................. 241/2 |
| 2004/0035964 | A1 | * | 2/2004 | Roggero ...................... 241/169 |
| 2007/0082389 | A1 | | 4/2007 | Clark et al. |
| 2007/0148756 | A1 | | 6/2007 | Bullen et al. |
| 2011/0186672 | A1 | | 8/2011 | Bougy |

FOREIGN PATENT DOCUMENTS

| EP | 0723009 A1 | 7/1996 |
|---|---|---|
| JP | 51-70870 | 6/1976 |
| JP | 04-340969 A | 11/1992 |
| JP | 06-341938 A | 12/1994 |

(Continued)

OTHER PUBLICATIONS

Search Report dated Nov. 25, 2011 from the European Patent Office in counterpart European application No. 11178751.1.

(Continued)

*Primary Examiner* — Faye Francis
(74) *Attorney, Agent, or Firm* — Sughrue Mion, PLLC

(57) ABSTRACT

A cell isolation apparatus includes: a chamber body which includes a chamber into which tissue is to be introduced; an isolation member which is moved in the chamber and which is to collide with the tissue to isolate a cell; and a controlling portion which controls an operation of the isolation member in the chamber body.

8 Claims, 10 Drawing Sheets

(56) References Cited

FOREIGN PATENT DOCUMENTS

| | | |
|---|---|---|
| JP | 08-053198 A | 2/1996 |
| JP | 8-280376 A | 10/1996 |
| JP | 2007-505631 A | 3/2007 |
| JP | 2009-005604 A | 1/2009 |
| JP | 2010-524498 A | 7/2010 |
| WO | WO 2005012480 A2 | 2/2005 |
| WO | WO 2005030936 A1 | 4/2005 |
| WO | WO 2005047866 A1 | 5/2005 |
| WO | 2008133874 A1 | 11/2008 |
| WO | WO 2009103868 A1 | 8/2009 |

OTHER PUBLICATIONS

Office Action, Issued by the Japanese Patent Office, Dated Aug. 19, 2014, In counterpart Japanese Application No. 2010-191035.

* cited by examiner

FIG. 12

| | | The number of isolated cells (×10⁴ cells/mg) | CK Activities (U/1.2 × 10⁶ cells) | Viability of cardiomyocytes (%) |
|---|---|---|---|---|
| TECHNIQUE OF INVENTION (200rpm, 30min) | mean | 9.72 | 488.40 | 98.50 |
| | std | 1.80 | 24.99 | 0.29 |
| RELATED-ART TECHNIQUE (50min) | mean | 5.97 | 459.25 | 95.52 |
| | std | 1.14 | 107.78 | 1.14 |

CELL ISOLATION APPARATUS

BACKGROUND OF THE INVENTION

The present invention relates to a cell isolation apparatus which is used in the field of clinics/research of regenerative medicine, or that of cell culture, and more particularly to a cell isolation apparatus which can isolate cells from tissue (body tissue) with a high survival rate.

In order to obtain living cells, tissue is minced with a sharp blade, and the minced tissue is subjected to enzymatic treatment with collagenase or the like to digest the extracellular matrix, thereby obtaining isolated cells.

In the related-art technique, in the enzymatic treatment with collagenase solution, procedures of enzymatic treatment and cell retrieving are repeated. Therefore, the related-art technique requires a very long time period. The related-art technique has further problems such as that the cell retrieving rate is dispersed because of differences in the mincing process with using a blade, the permeation rate in the enzymatic treatment, etc.

A related-art tissue dissociation device in which tissue is dissociated by rotation includes a container having a sterile interior for holding the tissue to be dissociated and a liquid medium, and also a dissociation element, inside the container, for engaging the tissue to cause dissociation of the tissue. The device further includes a resistive element, inside the container, for resisting movement of the tissue in response to the engagement by the dissociation element. In the device, relative motion between the dissociation element and the resistive element, and resistance provided by the resistive element as a result of the motion allow the dissociation element to effectively dissociate the tissue. A powered tissue dissociation device includes a power source operatively connected to the dissociation element for causing the dissociation element to move into engagement with the tissue (see JP-T-2007-505631).

In the related-art device, however, the resistance provided by the resistive element allows the dissociation element to effectively dissociate the tissue, and hence cells collide with the resistive element, thereby causing the possibility that the survival rate of cells is lowered.

SUMMARY

It is therefore an object of the invention to provide a cell isolation apparatus which can isolate cells from tissue (body tissue) with a high survival rate.

It is another object of the invention is to provide a cell isolation apparatus in which the operation time period can be remarkably shortened.

In order to achieve the object, according to the invention, there is provided a cell isolation apparatus comprising: a chamber body which includes a chamber into which tissue is to be introduced; an isolation member which is moved in the chamber and which is to collide with the tissue to isolate a cell; and a controlling portion which controls an operation of the isolation member in the chamber body.

The isolation member may include a plurality of blade members.

The cell isolation apparatus may further include a liquid level sensor which detects a level of a solution in the chamber. The controlling portion may control the operation of the isolation member based on a result of detection by the liquid level sensor.

The cell isolation apparatus may further include a temperature controlling unit which controls one of a temperature in the chamber body and a temperature of the cell isolation apparatus.

The cell isolation apparatus may further include a liquid introducing portion which introduces liquid into the chamber body.

The isolation member may include a shaft member, a plurality of blade members which are attached to the shaft member, and a supporting unit which supports the plurality of blade members in the shaft member.

The shaft member may be rotated by a magnetic rotation driving portion which is not in contact with the isolation member.

A bearing which receives the shaft member may be provided in the chamber body.

BRIEF DESCRIPTION OF THE DRAWINGS

FIG. 12 is a view showing the graphs of FIGS. 9 to 11 by means of numerals.

DETAILED DESCRIPTION OF EMBODIMENTS

Figure 1:
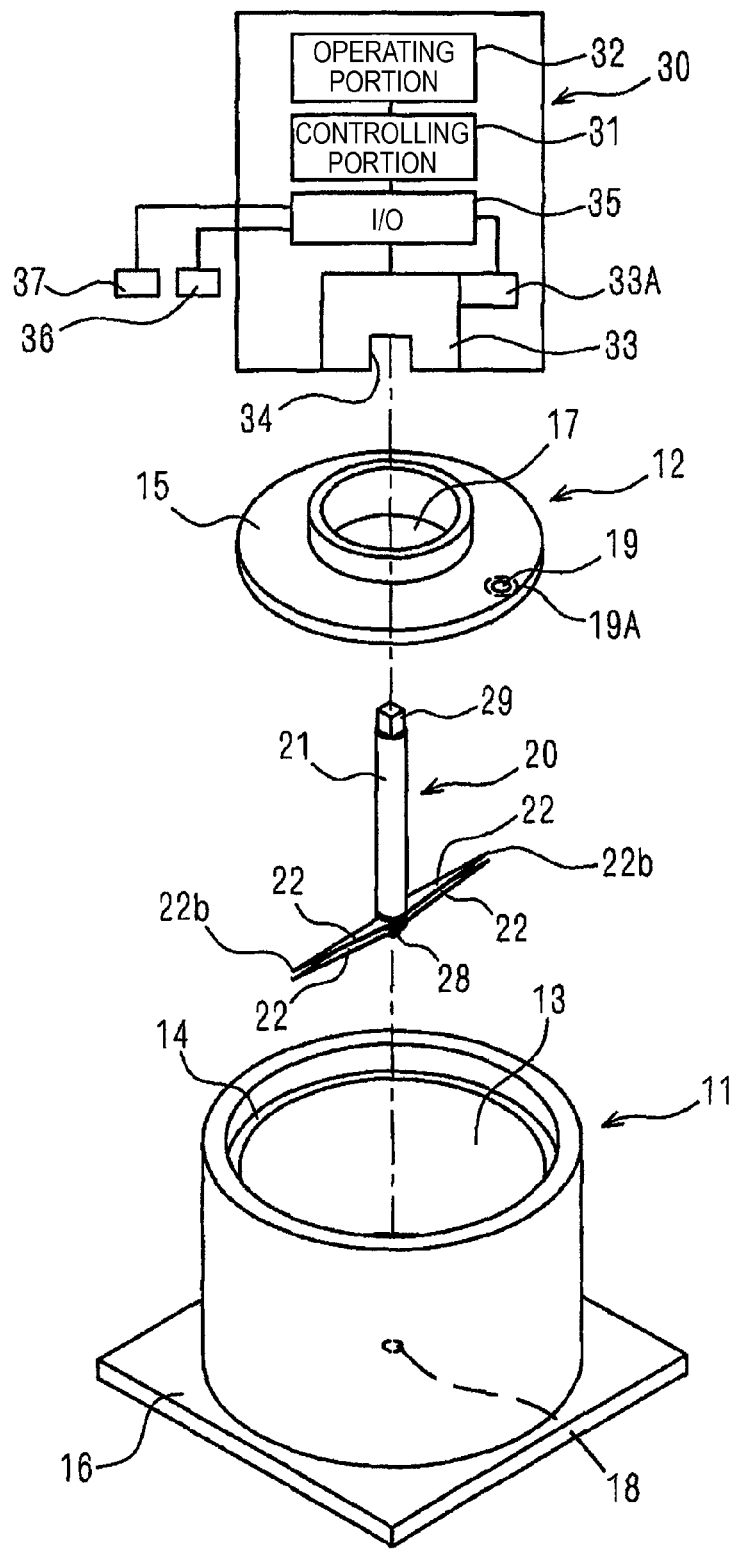
FIG. 1 is an assembly perspective view showing a first embodiment of the cell isolation apparatus of the invention.
Figure 2:
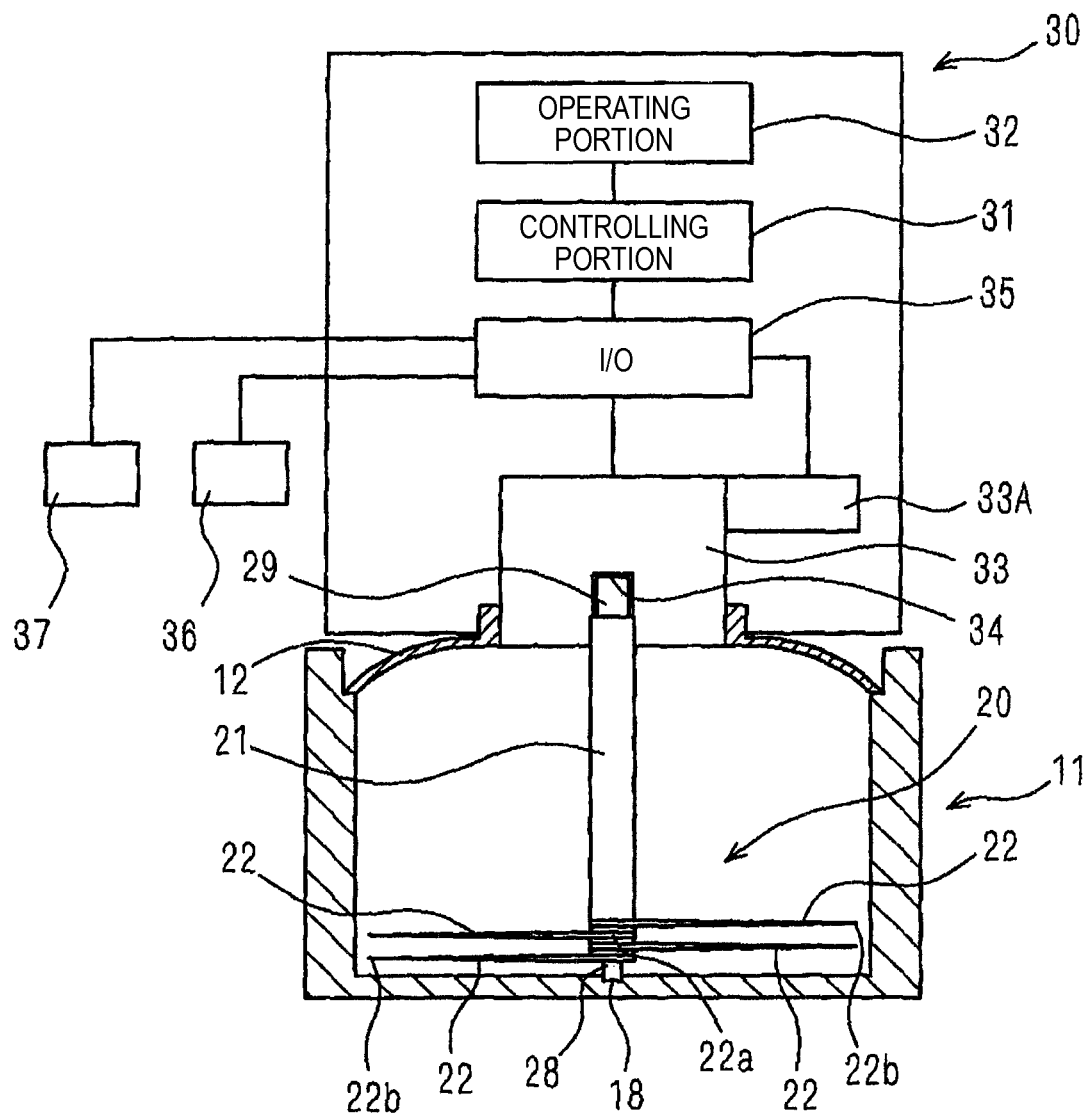
FIG. 2 is a view showing the first embodiment of the cell isolation apparatus of the invention, as viewed from a lateral side.

Hereinafter, embodiments of the cell isolation apparatus of the invention will be described with reference to the accompanying drawings. In the figures, the identical components are denoted by the same reference numerals, and duplicated description will be omitted. FIG. 1 is an assembly perspective view a cell isolation apparatus of a first embodiment, and FIG. 2 is a view of an assembled state, as viewed from a lateral side.

The cell isolation apparatus includes a cup-shaped chamber body 11, a lid member 12 for the chamber body 11, an isolation member 20, and a control device 30.

The chamber body 11 has a chamber 13 into which tissue is to be introduced, and in which the isolation member 20 is moved. A step 14 is formed in the inner peripheral wall of an opening portion of the chamber body 11. A peripheral edge portion 15a of a lid plate 15 of the lid member 12 is butted against and placed on the step 14. A flange 16 is disposed in a lower portion of the chamber body 11 so that the cell isolation apparatus can be stably installed.

Figure 3:
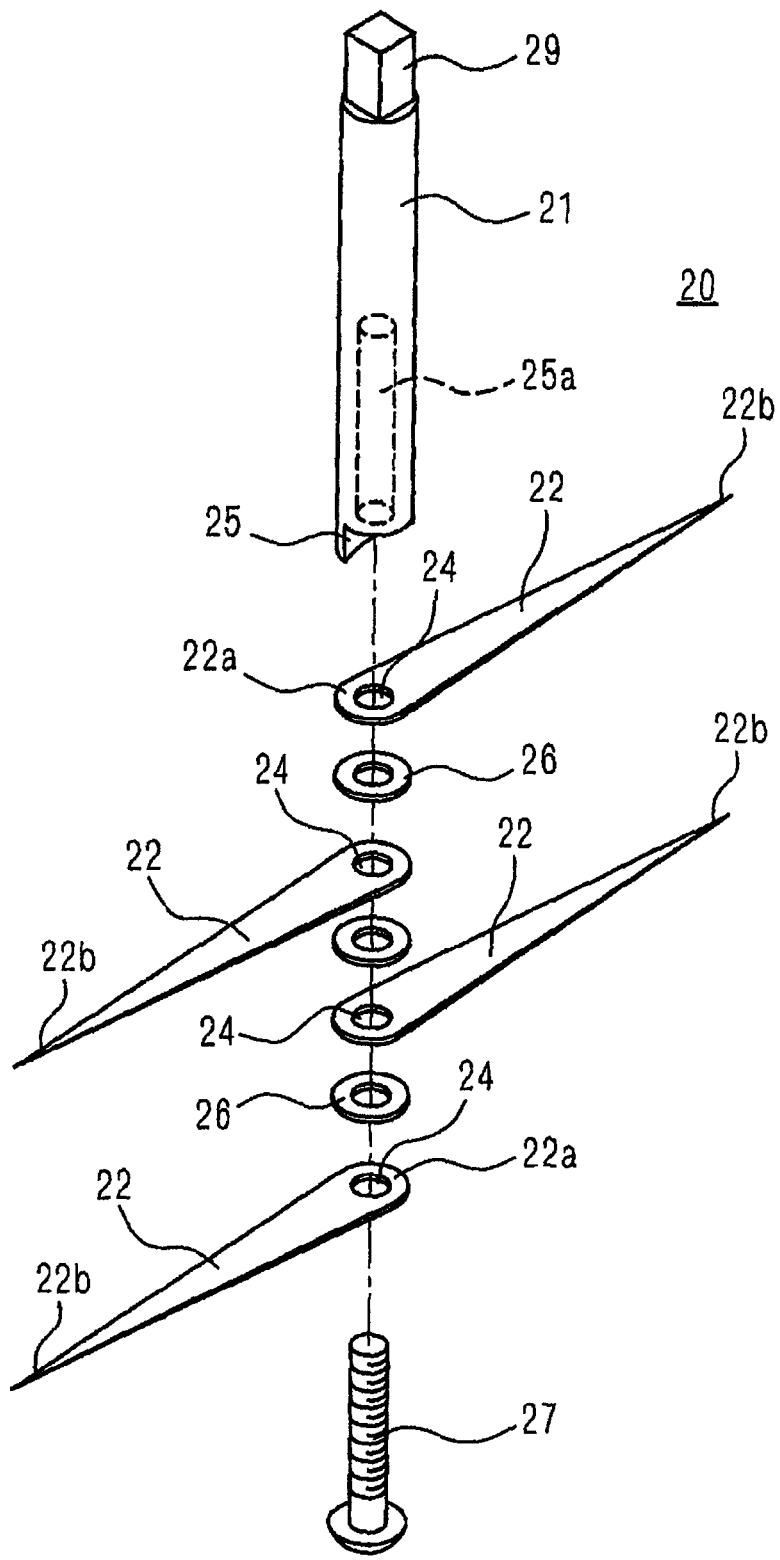
FIG. 3 is an assembly perspective view showing an isolation member in the first embodiment of the cell isolation apparatus of the invention.

As shown in FIG. 3, the isolation member 20 includes: a shaft member 21 which is a rotation shaft; a plurality of blade members 22 which are coupled to the shaft member 21; and a supporting unit which supports the plurality of blade members 22 in the shaft member 21. Each of the blade members 22 is formed so as to be gradually narrowed in width as advancing from a basal portion 22a to a tip end portion 22b. The blade member 22 has a planar shape of an acute isosceles triangle. A blade is formed in one or both of the long sides. In the basal portion 22a, a hole 24 is opened in the thickness direction.

A recess 25 which houses the basal portions 22a of the blade members 22 is formed in the vicinity of a lower end portion of the shaft member 21. A screw hole 25a is formed from the recess 25 into the shaft member 21 in the axial direction. In the embodiment, four blade members 22 are alternately stacked on one another through spacers 26, and tip end portions 22b of two of the blade members are in direction separated by 180 degrees from those of the other two blade members. The blade members 22 which are stacked in this state are supported by screwing a screw 27 through the holes 24 of the blade members 22 and the spacers 26 into the screw hole 25a of the shaft member 21. As described above, the recess 25, the screw hole 25a, the spacers 26, and the screw 27 constitute a supporting unit which supports the plurality of blade members 22.

Figure 4:
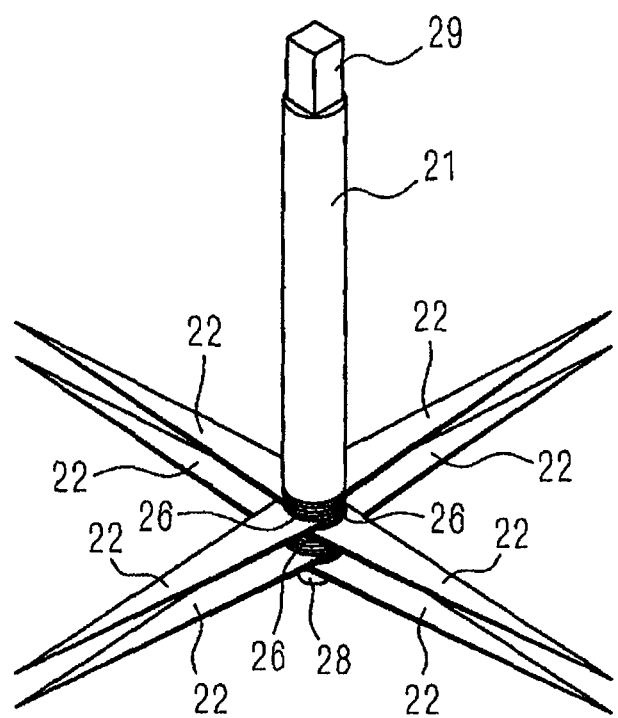
FIG. 4 is a perspective view showing a modification of the isolation member in the first embodiment of the cell isolation apparatus of the invention.

The above-described number and projected directions of the blade members 22 are mere examples. As shown in FIG. 4, therefore, the isolation member may include blade members 22 which are projected in directions separated by 90 degrees.

An upper end portion of the shaft member 21 is formed as a rectangular columnar coupling portion 29 which is coupled to a bearing hole 34 coupled to a motor 33 of the control device 30. A through hole 17 through which the shaft member 21 is passed is formed in a middle portion of the lid member 12. The coupling portion 29 of the shaft member 21 is coupled to the bearing hole 34 through the through hole 17.

A recess 18 which constitutes a bearing that receives a lower end portion 28 of the shaft member 21 is formed in a middle portion of the bottom surface of the chamber 13 of the chamber body 11. In a state where the apparatus is assembled, the lower end portion 28 of the shaft member 21 is rotatably supported by the recess 18. In this state, the blade members 22 are at positions which are slightly upward separated from the bottom surface of the chamber 13 of the chamber body 11, and, when rotated, collide with tissue so that the tissue can be adequately isolated.

In the lid member 12, a hole 19 which constitutes a liquid introducing portion for introducing liquid into the chamber body 11 is formed. In the hole 19, a lid piece 19A which is configured by an elastic member, and which, when pressed from the outside, is moved to cause the outside to communicate with the interior of the chamber body 11 through the hole 19 is disposed on the side of the interior of the chamber body 11. When the action of enzyme is to be stopped, therefore, a dropper into which an inhibitor or the like is sucked is inserted into the hole 19 that is normally closed by the lid piece 19A, and necessary liquid introduction can be performed.

The control device 30 includes a controlling portion 31 which is configured by a CPU for controlling the cell isolation apparatus. An operating portion 32 including various keys and the like, and an I/O 35 are connected to the controlling portion 31. The motor 33, a rotation sensor 33A, a temperature element 36 including a temperature sensor, and a liquid level sensor 37 are connected to the I/O 35.

The rotation sensor 33A is connected to the motor 33, detects the number of rotations and the rotational direction, and transmits them to the controlling portion 31. The temperature element 36 is disposed on the outer or inner wall surface of the chamber body 11, and functions as a temperature controlling unit which transmits the temperature to the controlling portion 31, and which performs a heating or cooling operation to control the temperature in response to the control by the controlling portion 31. For example, the liquid level sensor 37 is attached to a surface of the lid member 12 on the interior side of the chamber body 11, detects the level data (the distance from the attached position to the liquid level) of the liquid level on the side bottom surface of the chamber body 11, and transmits the data to the controlling portion 31.

The thus configured cell isolation apparatus can perform the cell isolation process in the following manner. A predetermined amount of an enzyme solution which is previously heated to the activation temperature is introduced into the chamber body 11. Next, tissue extracted from a living body is loaded into the chamber body 11. The isolation member 20, the lid member 12, and the control device 30 are set to predetermined positions to assemble the cell isolation apparatus. The stirring conditions (the number of rotations, the rotating method, the time, and the like), and the temperature conditions are set through the operating portion 32, and a key for starting the process is operated. In the rotating method, right rotation for aa sec., stop for bb sec., left rotation for cc sec., and the like are set. The time period for repeating the method is input.

The controlling portion 31 controls the rotation of the motor 33 in accordance with the above-described input, and the temperature element 36 in accordance with the temperature conditions to maintain a predetermined temperature. In the case where variation for a predetermined time period exceeds a predetermined threshold as a result of the detection by the liquid level sensor 37, the adequate stirring state is realized by, for example, lowering the number of rotations, and cells are isolated with a high survival rate.

The turbid solution which has been processed as described above is taken out from the chamber body 11, and then subjected to the mesh process to take out isolated cells.

Next, the configuration of a cell isolation apparatus of a second embodiment will be described. The main components of the cell isolation apparatus are a cup-shaped chamber body 11A, a lid member 12A of the chamber body 11A, an isolation member 20A, and a control device 30A.

Figure 5A:
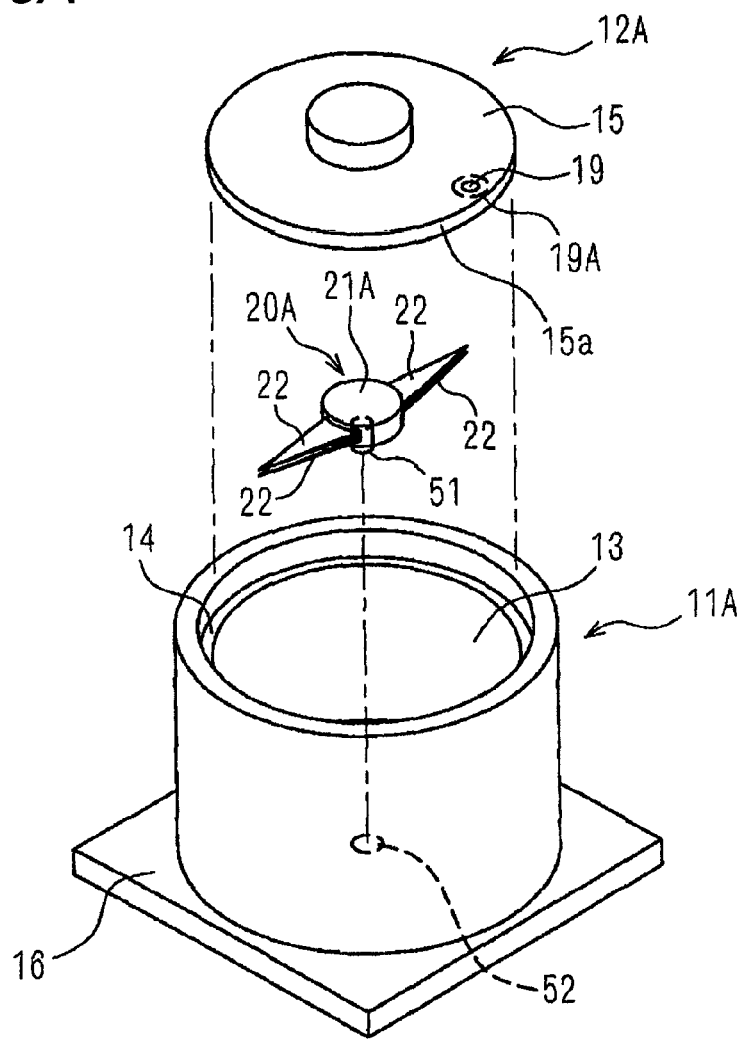
FIG. 5A is an assembly perspective view showing a second embodiment of the cell isolation apparatus of the invention.

FIG. 5A is an assembly perspective view. A shaft member 21A of the isolation member 20A has a flat columnar shape, and includes a small columnar shaft 51 which is projected from the lower surface. A bearing 52 which rotatably supports the shaft 51, and which is configured by a bottomed hole is formed in a middle portion of the bottom surface of a chamber 13 of the chamber body 11A.

Figure 7:
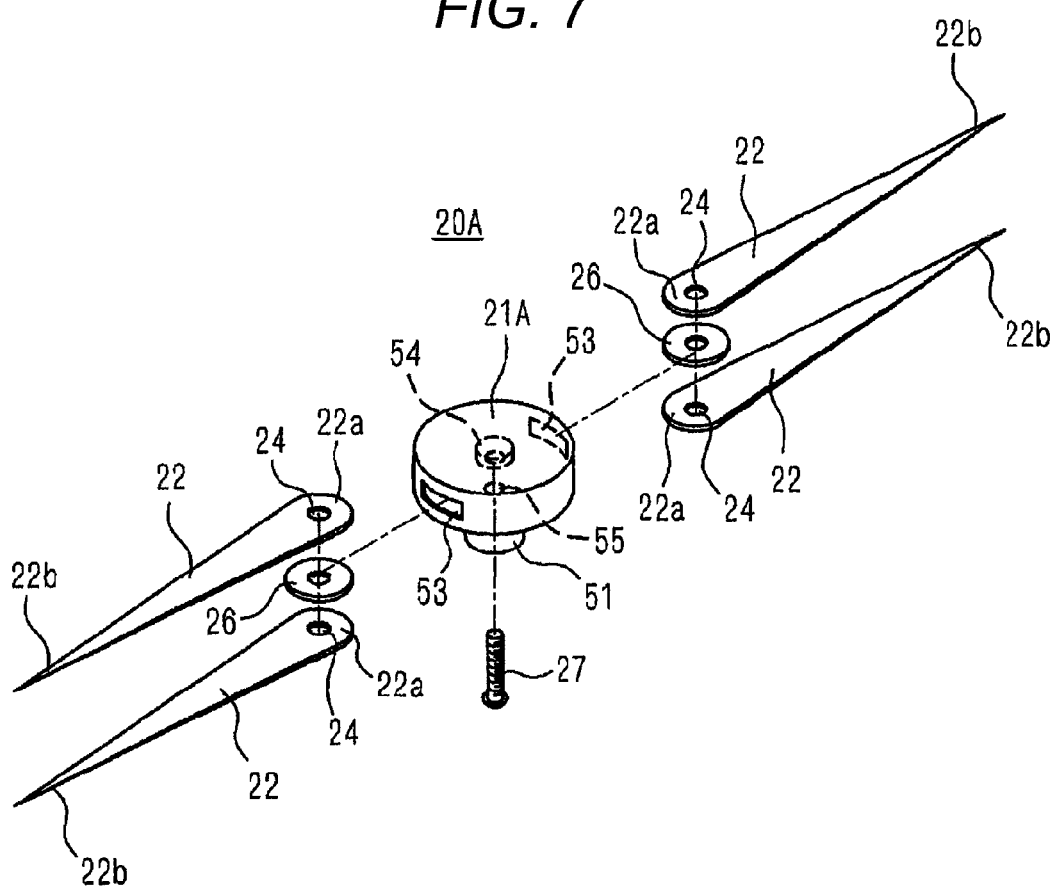
FIG. 7 is an assembly perspective view showing an isolation member in the second embodiment of the cell isolation apparatus of the invention.

FIG. 7 is an assembly perspective view of the isolation member 20A. Openings 53 into which the basal portions 22a of the blade members 22 are inserted are formed at positions in a side portion of the shaft member 21A which are paired in the diameter direction. A screw hole 54 which is not passed through the surface is formed in a middle portion of a top portion of the shaft member 21A.

Two blade members 22 are inserted into each of the openings 53 while being stacked on each other through the spacer 26. A hole 55 which is passed through the surface is formed in a middle portion of a lower portion of the shaft member 21A. In the total of four blade members 22 which are inserted through the two openings 53, the screw 27 is passed through the holes 24 via the hole 55 to be screwed with the hole 24, thereby constituting a supporting unit which supports the plurality of blade members 22.

Figure 8:
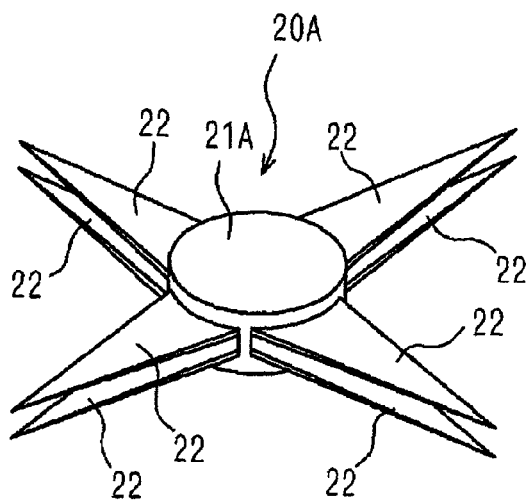
FIG. 8 is a perspective view showing a modification of the isolation member in the second embodiment of the cell isolation apparatus of the invention.

The above-described number and projected directions of the blade members 22 are mere examples. As shown in FIG. 8, therefore, the isolation member may include blade members 22 which are projected in directions separated by 90 degrees.

Figure 5B:
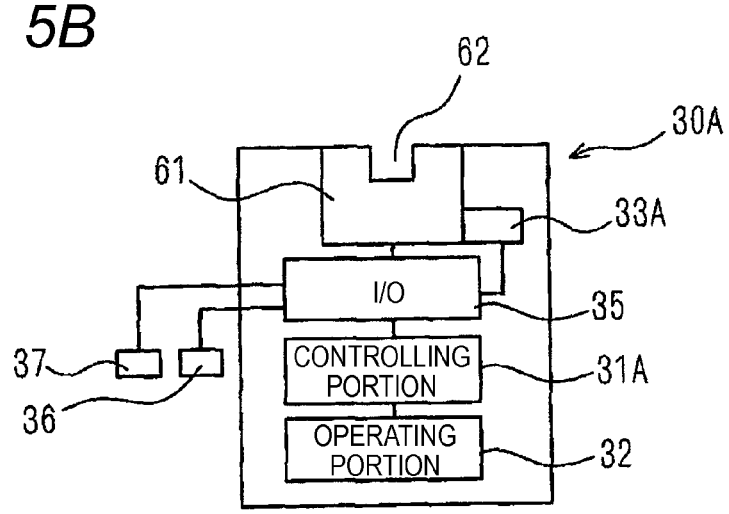
FIG. 5B is a view showing the second embodiment of the cell isolation apparatus of the invention, as viewed from a lateral side.
Figure 6:
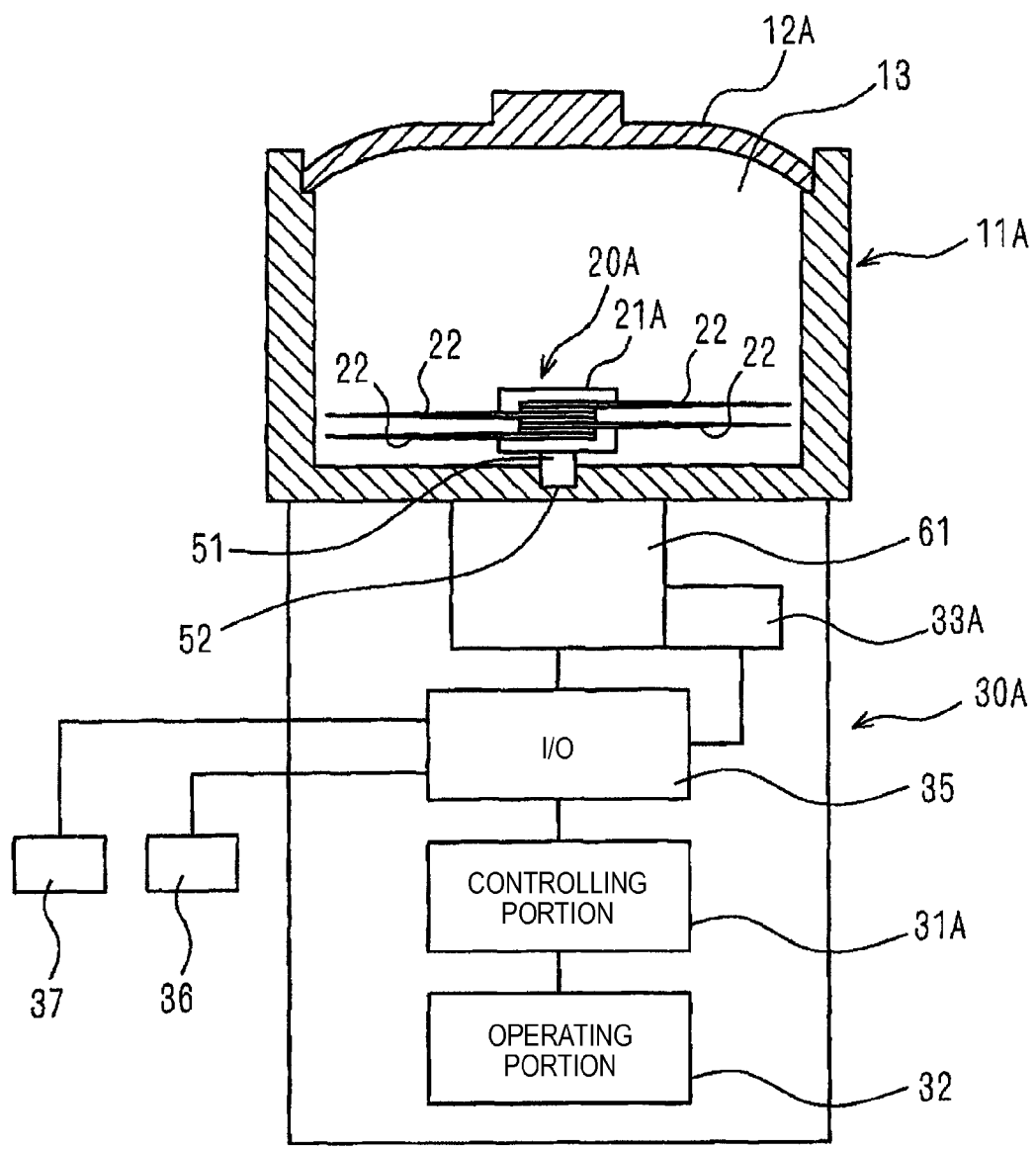
FIG. 6 is a view showing the second embodiment of the cell isolation apparatus of the invention, as viewed from a lateral side.

As shown in FIG. 5B and FIG. 6, a stirrer driving device 61 is disposed below the chamber body 11A. In the embodiment, a configuration where the stirrer driving device 61 is incorporated in the control device 30A is shown. However, the components other than the stirrer driving device 61 may be disposed at other positions. A coupling groove 62 for the chamber body 11A is formed on the case of the control device 30A, and fitted with a projection (not shown) of the chamber body 11A to be fixed thereto.

The control device 30A is configured in the same manner as that of the first embodiment except that a controlling portion 31A controls the stirrer driving device 61 to control the rotation of the shaft member 21A which constitutes a rotor of a stirrer. According to the configuration, the shaft member 21A is rotated as a rotor by the stirrer driving device 61 that is a magnetic rotation driving portion which is not in contact with the isolation member 20A.

The thus configured cell isolation apparatus can perform the cell isolation process in the following manner. A predetermined amount of an enzyme solution which is previously heated to the activation temperature is introduced into the chamber body 11A. Next, tissue extracted from a living body is loaded into the chamber body 11A. The isolation member 20A, the lid member 12A, and the control device 30A are set to predetermined positions to assemble the cell isolation apparatus. In this state, the chamber 13 of the chamber body 11A is isolated from the outside, and can be set to be in a hermetically-sealed state. As a result, the risk that unwanted substances enter the chamber body 11A is eliminated, and there is no possibility that the liquid or the like in the chamber body 11A is splashed out to the outside.

In the same manner as the first embodiment, the stirring conditions and the temperature conditions are set through the operating portion 32, and a key for starting the process is operated, the process is performed under control of the controlling portion 31A, and the turbid solution is taken out from the chamber body 11A, and then subjected to the mesh process to take out isolated cells.

By using the cell isolation apparatus of the above-described first or second embodiment, cells were isolated from tissue. In this case, cells which were obtained by a related-art technique, and those which were obtained by the invention were compared with each other. Cardiomyocyte tissue of a neonate rat was used as the tissue. With respect to the stirring conditions, the number of rotations was 200 rpm, and an intermittent operation of rotation for 0.5 sec. and stop of 1 sec. was performed for 30 min. A mesh of 40 μm was used.

Figure 9:
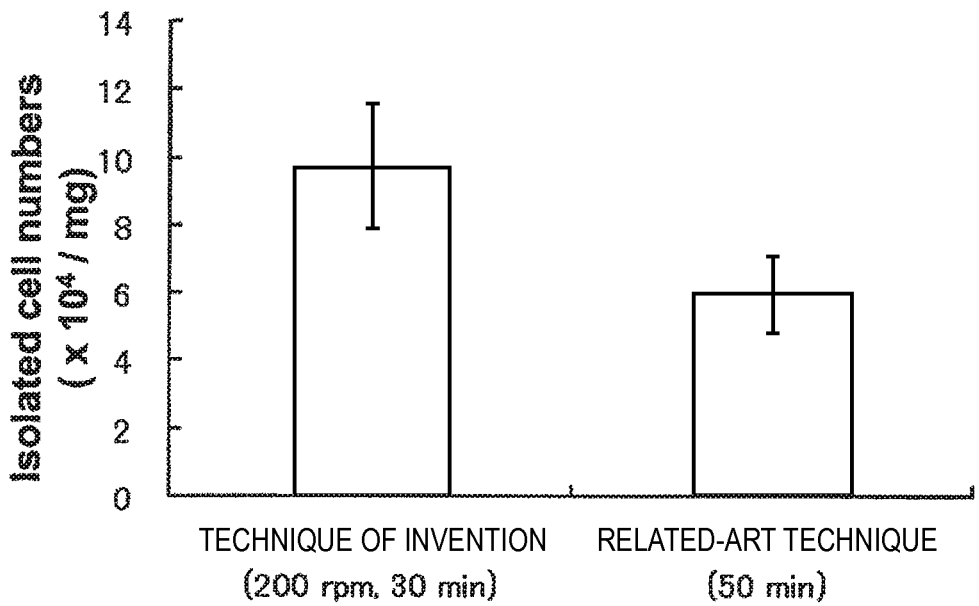
FIG. 9 is a view showing a graph of the acquired amount of cells which were obtained by the technique of the invention and a related-art technique.

FIG. 9 shows a graph in which the mean value and the standard deviation of acquired amounts of cells that were acquired from the same amount of tissue were obtained by the technique of the invention and a related-art technique. FIG. 12 shows the mean value and the standard deviation in the form of numerals. As apparent from FIGS. 9 and 12, the technique of the invention can obtain cells with very high efficiency.

Figure 10:
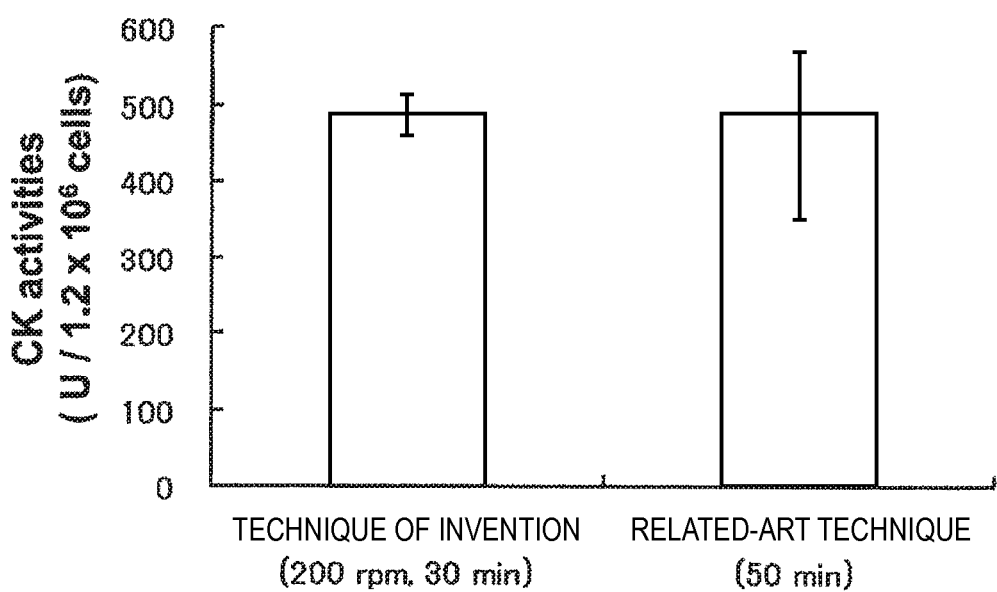
FIG. 10 is a view showing a graph of the activity value of creatin kinase (CK) per unit number of cells immediately after acquisition of isolated cells which were obtained by the technique of the invention and a related-art technique.

FIG. 10 shows a graph in which the mean value and the standard deviation of the CK activity value per unit number of cells immediately after acquisition of isolated cells were obtained by the technique of the invention and a related-art technique. FIG. 12 shows the mean value and the standard deviation in the form of numerals. As apparent from FIGS. 10 and 12, the rate of cardiomyocyte cells per unit number of cells can be known. In the technique of the invention, damage to cells can be reduced, and therefore it is known that living cardiomyocyte cells can be easily acquired in a more excellent manner as compared with the related-art technique.

Figure 11:
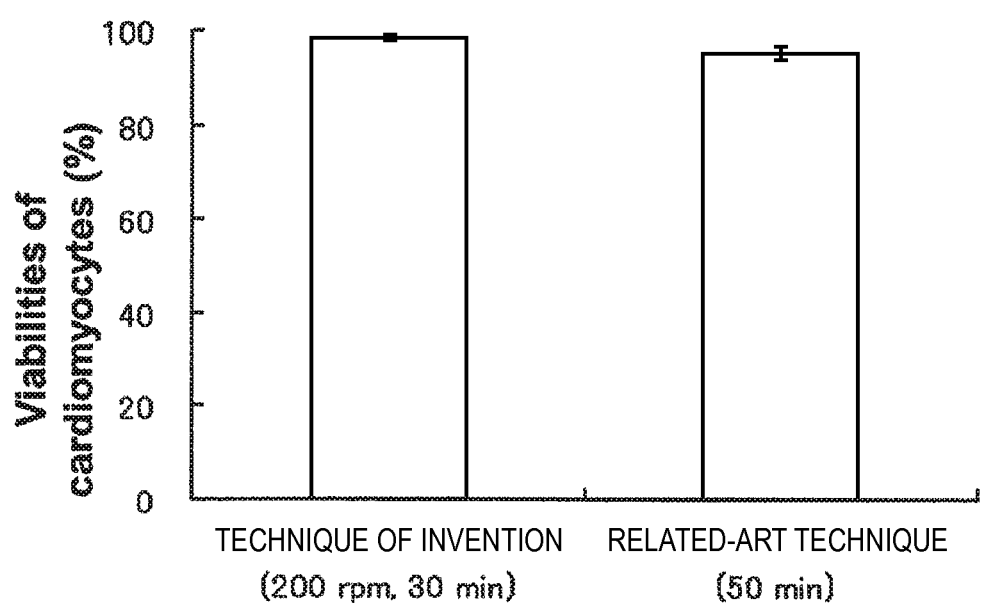
FIG. 11 is a view showing a graph of the survival rate of cells on the fourth day after acquisition of isolated cells which were obtained by the technique of the invention and a related-art technique.

FIG. 11 shows a graph in which the mean value and the standard deviation of the survival rate of cells on the fourth day after acquisition of isolated cells were obtained by the technique of the invention and a related-art technique. FIG. 12 shows the mean value and the standard deviation in the form of numerals. As apparent from FIGS. 11 and 12, it is known that, in the technique of the invention, less damage is imparted to cells, and cells can be acquired with a higher survival rate as compared with the related-art technique.

According to an aspect of the invention, the cell isolation apparatus includes the chamber body having the chamber into which tissue is to be introduced, and in which the isolation member is moved, and the operation of the isolation member in the chamber body is controlled. Therefore, the survival rate of cells can be enhanced.

According to an aspect of the invention, the isolation member has a plurality of blade members, and hence isolation of cells can be efficiently performed.

According to an aspect of the invention, the cell isolation apparatus includes the liquid level sensor which detects the level of the solution in the chamber, and the controlling portion controls the operation of the isolation member based on a result of detection by the liquid level sensor. Therefore, stirring can be adequately performed without causing the solution in the chamber to bubble, and the survival rate of cells can be enhanced.

According to an aspect of the invention, the cell isolation apparatus includes the temperature controlling unit which controls the temperature in the chamber body, or that of the apparatus. Therefore, activation/deactivation of enzyme can be controlled.

According to an aspect of the invention, the cell isolation apparatus includes the liquid introducing portion for introducing liquid into the chamber body. When the action of enzyme is to be stopped, therefore, necessary liquid introduction such as introduction of an inhibitor can be performed.

According to an aspect of the invention, the isolation member includes the shaft member, the plurality of blade members which are coupled to the shaft member, and the supporting unit which supports the plurality of blade members in the shaft member. Therefore, an adequate stirred state can be realized by necessary rotation, and the survival rate of cells can be enhanced.

According to an aspect of the invention, the shaft member is rotated by the magnetic rotation driving portion which is not in contact with the isolation member. Therefore, stirring can be performed while the chamber body is covered by a lid, and there is an effect that it is possible to prevent unwanted substances from entering the chamber body from the outside, and also to prevent the outside from being contaminated.

According to an aspect of the invention, the bearing for receiving the rotation shaft is formed in the chamber body. Therefore, stable rotation can be ensured in the chamber body.

What is claimed is:

1. A cell isolation apparatus comprising:
    a chamber body which includes a chamber into which tissue is to be introduced;
    an isolation member which is moved in the chamber and which is to collide with the tissue to isolate a cell;
    a controlling portion which controls an operation of the isolation member in the chamber body, and
    a liquid level sensor which detects a level of a solution in the chamber,
    wherein the controlling portion controls the operation of the isolation member based on a result of detection by the liquid level sensor, and
    the isolation of the cell provides a high survival rate of the cell.

2. The cell isolation apparatus according to claim 1, wherein the isolation member includes a plurality of blade members.

3. The cell isolation apparatus according to claim 1, further comprising:
    a temperature controlling unit which controls one of a temperature in the chamber body and a temperature of the cell isolation apparatus.

4. The cell isolation apparatus according to claim 1, further comprising:
    a liquid introducing portion which introduces liquid into the chamber body.

5. The cell isolation apparatus according to claim 1, wherein
    the isolation member includes a shaft member, a plurality of blade members which are attached to the shaft member, and a supporting unit which supports the plurality of blade members in the shaft member.

6. The cell isolation apparatus according to claim 5, wherein the shaft member is rotated by a magnetic rotation driving portion which is not in contact with the isolation member.

7. The cell isolation apparatus according to claim 5, wherein a bearing which receives the shaft member is provided in the chamber body.

8. The cell isolation apparatus according to claim 1, wherein the controlling portion controls the operation of the isolation member according to a variation of a predetermined time period exceeds a predetermined threshold as a result of the detection of the liquid level sensor.

* * * * *